United States Patent [19]

Alexander et al.

[11] Patent Number: 4,677,174

[45] Date of Patent: Jun. 30, 1987

[54] WATER ABSORBENT STYRENE-ACRYLIC ACID COPOLYMERS

[75] Inventors: William Alexander, Naperville; Barbara R. Regan, Glenview; Mark Anderson, Wheaton, all of Ill.

[73] Assignee: American Colloid Company, Arlington Heights, Ill.

[21] Appl. No.: 854,000

[22] Filed: Apr. 21, 1986

[51] Int. Cl.[4] ............................................. C08F 230/04
[52] U.S. Cl. ................................. 526/240; 526/317.1; 252/194
[58] Field of Search .............................. 526/240, 317.1

[56] References Cited

U.S. PATENT DOCUMENTS 4,342,858  8/1982  Herman et al. ..................... 526/240
4,552,938  11/1985  Mikita et al. ....................... 526/240

Primary Examiner—Joseph L. Schofer
Assistant Examiner—Peter F. Kulkosky
Attorney, Agent, or Firm—Mason, Kolehmainen, Rathburn & Wyss

[57] ABSTRACT

Water absorbing, cross-linked acrylate resin copolymers are prepared by aqueous polymerization of (A) acrylic acid neutralized 70 to 100 mole percent for example with ammonia, and/or caustic alkali and/or an amine; with (B) styrene and/or methyl methacrylate in an amount of 1% to 25% based on the weight of acrylic acid or acrylate, and (C) acrylamide in a mole ratio of 70 to 100 mole percent (A) to 30:0 mole percent (C); and (D) a water miscible or a water soluble polyvinyl monomer in an amount of 0.001 to 0.3 weight percent based on the total weight of (A), (B), (C) and (D).

16 Claims, 4 Drawing Figures

FIG. 1
NO STYRENE

FIG. 2
2% STYRENE

FIG. 3
4% STYRENE

FIG. 4
6% STYRENE

WATER ABSORBENT STYRENE-ACRYLIC ACID COPOLYMERS

FIELD OF THE INVENTION

The present invention relates to a method of manufacturing polyacrylate copolymer resins having improved water absorbing properties and more particularly to an improved process of preparing cross-linked copolymers of acrylic acid, styrene and/or methyl methacrylate, and polyvinyl monomers.

BACKGROUND OF THE INVENTION

Water absorbing resins have found wide use in sanitary goods, hygenic goods, water retaining agents, dehydrating agents, sludge coagulants, thickening agents, condensation preventing agents and release control agents for various chemicals. Water absorbing resins heretofore known include hydrolysis products of starch-acrylonitrile graft polymers, carboxymethylcellulose, cross-linked polyacrylate products and other resins such as polyvinyl alcohol, polyethylene oxide and polyacrylonitrile resins. Of these water absorbing resins, the hydrolysis products of starch and acrylonitrile graft polymers have comparatively high ability to absorb water but require a cumbersome process for production and have the drawbacks of low heat resistance and decaying or decomposing easily due to the presence of starch.

One of the processes for polymerizing acrylic acid and acrylates is aqueous solution polymerization. The polymer obtained by this process is soluble in water and, therefore, is cross-linked to modify the polymer into a useful water absorbing resin. However, even if the modification is effected by reacting a cross-linking agent concurrently with or after aqueous solution polymerization, the resulting reaction product is in the form of a highly viscous aqueous solution or a gel containing absorbed water which is difficult to handle. Thus, the aqueous solution or gel must be dehydrated (dried) to obtain a water absorbing resin in the desired solid or powder form. It is nevertheless difficult to dry the reaction product efficiently by the usual rotary drum roller method or spray drying method because care must be taken to avoid excessive cross-linking which results from over-heating during drying and insufficient drying results in reduced cross-linking density. Extreme difficulties are therefore encountered in preparing a product of a desired low water content and good water absorbing ability.

SUMMARY OF THE INVENTION

An object of the present invention is to provide a process for preparing a water absorbing cross-linked acrylate resin copolymer of low water content by aqueous solution polymerization without any additional dehydrating or drying step.

Another object of the present invention is to provide a process for preparing a cross-linked polyacrylate resin copolymer by copolymerization of partially or fully neutralized acrylic acid; a styrene and/or methyl methacrylate monomer; and a water-miscible to water soluble polyvinyl monomer in a combined concentration of 30 to 80% by weight partially or fully neutralized acrylic acid and 1% to 25% styrene and/or methyl methacrylate, based on the weight of acrylic acid, in water and initiating polymerization.

Another object of the present invention is to provide a process for preparing a cross-linked polyacrylate resin copolymer by copolymerization of acrylic acid neutralized 70–100 mole percent, with styrene and/or methyl methacrylate and a polyvinyl monomer in proportions of 30 to 80% by weight partially or fully neutralized acrylic acid; 1 to 25% based on the weight of acrylic acid, of styrene and/or methyl methacrylate and 0% to 30% by weight acrylamide, based on the weight of acrylic acid, in aqueous solution.

Another object of the present invention is to provide a process for producing a polyacrylate resin copolymer cross-linked with 0.2 weight percent to 0.6 weight percent based on the weight of monomers, of a water miscible or water soluble polyvinyl monomer cross-linking agent to achieve a "dry feel" to the resin after significant water absorption.

In brief, the present invention is directed to a process for preparing water absorbing, cross-linked acrylate resin copolymers by aqueous polymerization of (A) acrylic acid neutralized 70 to 100 mole percent for example with ammonia, and/or caustic alkali and/or an amine; with (B) styrene and/or methyl methacrylate in an amount of 1% to 25% based on the weight of acrylic acid or acrylate, computed as based on acrylic acid; and (C) acrylamide in a mole ratio of 70 to 100 mole percent (A) to 30:0 mole percent (C); and (D) a water miscible or a water soluble polyvinyl monomer in an amount of 0.001 to 0.3 weight percent based on the total weight of (A), (B), (C) and (D). To achieve the full advantage of the present invention the monomer concentration of (A), (B) and (C) is at least 50 wt. % of the aqueous solution. A "dry feel" is obtained at a polyvinyl monomer concentration of at least 0.2 wt. percent of the aqueous solution.

In accordance with an important embodiment of the present invention, a heated aqueous solution comprising (A) acrylic acid neutralized 70 to 100 mole percent, for example with ammonia, and/or caustic alkali and/or an amine; and (B) styrene and/or methyl methacrylate in an amount of 1% to 25% based on the amount of acrylic acid and acrylate, computed as based on acrylic acid; and (C) a water-miscible to water-soluble polyvinyl monomer, water and, when desired, an organic solvent having a boiling point of 40 to 150° C., and having a combined monomer concentration of (A) plus (B) plus (C) of 30 to 80 wt. % is subjected to copolymerization in the presence of a polymerization initiator without external heating while allowing water to evaporate off.

BRIEF DESCRIPTION OF THE DRAWINGS

The above and other objects and advantages of the present invention will become apparent from the following detailed description of the present invention taken in conjunction with the drawings, wherein.

DETAILED DESCRIPTION OF THE INVENTION

In accordance with the present invention a cross-linked polyacrylate resin copolymer is prepared by aqueous solution polymerization while dehydrating or drying the reaction product during polymerization by utilizing the exothermic heat from the copolymerization and cross-linking reactions for drying.

It has been found that acrylic acid neutralized in the range of 70 to 100 mole percent will copolymerize with styrene and/or methyl methacrylate and cross-link rapidly with a polyvinyl monomer cross-linking agent to drive away excess water leaving a solid water absorbing resin copolymer having a desired degree of polymerization as well as new and unexpected water absorbing capacity. One or more polymerization catalysts or initiators can be added to the aqueous monomer mixture to aid in polymerization.

According to the present invention, a hot aqueous solution is prepared first which comprises acrylic acid neutralized 70 to 100 mole percent; styrene and/or methyl methacrylate; a water-miscible or water-soluble polyvinyl monomer; water and, when desired, an organic solvent having a boiling point of 40° to 150° C., and which contains the acrylate monomer; styrene and/or methyl methacrylate; and the polyvinyl monomer in a combined concentration of 30 to 80 wt. %.

To achieve the full advantage of the present invention, the acrylate; styrene and/or methyl methacrylate; and polyvinyl monomers are present in a combined concentration of less that 70 weight percent of the monomer solution. In accordance with another important embodiment of the present invention, the combined concentration of the acrylate, styrene, methyl methacrylate and polyvinyl monomers is less than 55 weight percent of the monomer solution. The concentration of the monomers is deliberately determined considering the state of the solution (i.e., as to whether or not the monomers can be completely dissolved in water), ease of the reaction of the monomers, escape of the monomers due to the scattering during the reaction, and the like.

The aqueous solution can be prepared easily usually by placing acrylic acid, a strong alkali such as potassium hydroxide and/or ammonium hydroxide or a basic amine for neutralizing the acid, styrene and/or methyl methacrylate, and the polyvinyl monomer into water in such amounts that the resulting solution has the above-mentioned monomer concentration. To thoroughly mix the monomers, the mixture can be heated to an elevated temperature. Any strongly basic alkali metal compound can be used for neutralization of the acrylic acid, such as potassium hydroxide, sodium hydroxide, lithium hydroxide, cesium hydroxide, potassium carbonate or sodium carbonate. Although it is desirable to use the neutralizing agent usually in an amount sufficient to neutralize acrylic acid 100 mole %, there is no particular need to neutralize the acid 100% and the neutralizing agent, e.g., hydroxide, is used in such an amount as to achieve not less than about 70% neutralization. Accordingly, the aqueous solution may contain up to about 30 mole percent of free acrylic acid based on the amount of acrylic acid and acrylate. However, a large quantity of free acrylic acid, if present in the aqueous solution, is likely to partly splash out of the reaction vessel, resulting in a loss during the reaction, leading to a reduced degree of polymerization. Use of an excessive amount of the neutralizing agent will not raise any particular problem, but the excess does not participate in the polymerization reaction and is therefore useless.

We have also found that when the aqueous solution further contains an organic solvent having a boiling point of 40° to 150° C., the temperature of the aqueous solution is controllable with great ease and the resulting cross-linked resin copolymer has remarkably improved ability to absorb water at an initial rate.

When incorporating an organic solvent according to the invention, the aqueous monomer solution has a solidifying point which is about 10 to about 20° C. lower than otherwise. This increases the allowable range of temperature control at least about 3 times. The organic solvent used is vigorously evaporated along with water by the heat of polymerization of the monomers. Since the latent heat of the evaporation of the organic solvent is considerably smaller than that of water, the organic solvent functions as a blowing agent in the polymerization reaction system, consequently rendering the resulting resin porous. The resin exhibits about 2 to about 5 times higher initial rate of water absorption than the one obtained without using the organic solvent while possessing high water absorbing ability. Thus, the organic solvent, when added to the aqueous monomer solution, produces improved effects without in any way impairing the advantages resulting from the use of the monomer solution.

Examples of organic solvents to be used in the invention when desired and having a boiling point of 40° to 150° C. are methanol, ethanol, propanol and like alcohol solvents, acetone, methyl ethyl ketone and like detone solvents, cyclohexane, n-hexane, n-heptane and like hydrocarbon solvents, benzene, toluene and like aromatic hydrocarbon solvents, and tetrahydrofuran and like furan solvents. These solvents may be used singly or in admixture. The solvent is used in an amount of 0.5 to 15 wt. %, preferably 1 to 10 wt. %, based on the combined amount of the acrylic acid, styrene, methyl methacraylate and polyvinyl monomers. With less than 0.5 wt. % of the solvent present, a sufficient blowing action will not take place, while the solidifying point of the monomer solution will not lower greatly. Conversely if more than 15 wt. % of the solvent is used, the resulting resin is likely to exhibit reduced water absorbing ability although achieving a high initial rate of water absorption. Moreover the monomers are likely to separate out, hence objectionable. Because the monomer solution is heated prior to polymerization and further because the organic solvent evaporates along with water, the boiling point of the solvent is more preferably in the range of 55° to 120° C.

In accordance with the present invention, acrylic acid neutralized 70-100 mole percent is mixed with 1% to 25%, based on the weight of acrylic acid, styrene and/or methyl methacrylate; and a water-miscible or water-soluble polyvinyl monomer in an aqueous solution at a temperature of about 20° to 100° C. The solution is subjected to a polymerization reaction and a cross-linking reaction by the addition of a polymerization initiator. The polymerization reaction proceeds sufficiently within a very short period of time and if the monomer concentration is at least 30 percent by weight of the aqueous monomer mixture, the heat of the copolymerization and cross-linking reactions will evaporate water rapidly from the reaction system to form a dry solid (less than 15 percent by weight water) water absorbing resin without the need for any subsequent drying step. The solid can be easily pulverized into a powder suitable for any desired use.

According to an important embodiment of the present invention, a hot, i.e., at least 25° C., aqueous solution is prepared first including acrylic acid neutralized 70 to 100 mole percent; styrene and/or methyl methacrylate in an amount of 1% to 25% based on the weight of acrylic acid; optionally acrylamide; a water-miscible or water-soluble polyvinyl monomer; and water. The aqueous solution can be prepared easily by placing (A) acrylic acid, and an amine, and/or a caustic alkali and/or ammonia for neutralizing the acid; (B) styrene and/or methyl methacrylate in an amount of 1% to 25% based on the weight of acrylic acid; (C) acrylamide (0–30 mole percent based on acrylic acid); and (D) a polyvinyl monomer into water to form a mixed monomer solution. To dissolve the monomers thoroughly, the mixture can be heated to an elevated temperature up to the boiling point of water, i.e., 100° C.

The polyvinyl monomer to be used in accordance with the present invention should be miscible with or soluble in water so that the monomer will be uniformly dissolved or dispersed in the aqueous solution of the monomer mixture. Examples of such polyvinyl monomers include trimethylol propane triacrylate, bisacrylamides such as N,N'-methylenebisacrylamide and N,N'-methylenebismethacrylamide; polyacrylic (or polymethacrylic) acid esters represented by the following formula (I); and diacrylamides represented by the following formula (II). Among these, especially preferably are N,N'-methylenebisacrylamide, N,N'-methylenebismethacrylamide and like bisacrylamides.

Formula (I)

wherein X is ethylene, propylene, trimethylene, hexamethylene, 2-hydroxypropylene, (CH$_2$CH$_2$O)$_n$CH$_2$CH$_2$ -or n and m are each an integer of from 5 to 40, and k is 1 or 2.

The compounds of the forumula (I) are prepared by reacting polyols, such as ethylene glycol, propylene glycol, trimethylolpropane, 1,6-hexanediol, glycerin, pentaerythritol, polyethylene glycol and polypropylene glycol, with acrylic acid or methacrylic acid.

Formula (II)

wherein l is 2 or 3.

The compounds of the formula (II) are obtained by reacting polyalkylenepolyamines, such as diethylenetriamine and triethylenetetramine, with acrylic acid.

The polyvinyl monomer is used in an amount of about 0.001 to 0.3 wt. % based on the amount of acrylic acid, styrene, methyl methacrylate and acrylamide monomers in the aqueous monomer mixture. In accordance with an important embodiment of the present invention, the polyvinyl monomer cross-linking agent should be present in the aqueous solution in an amount of at least 0.2 wt. % based on the total weight of monomers to provide a resin sufficiently cross-linked to have a "dry feel" after significant water absorption. If the polyvinyl monomer is included in the aqueous solution in an amount of 0.2 to 0.6 weight percent based on the weight of neutralized acrylic acid and polyvinyl monomers, the resulting polymer will have an exceedingly "dry feel" on absorption of water.

The aqueous mixed monomer solution is heated and thereafter subjected to copolymerization and crosslinking reactions with the addition of a polymerization initiator. Although the temperature of the aqueous mixed monomer solution is not particularly limited since the mixed monomer solution is initiated into polymerization by the addition of the initiator, the temperature is usually about 50 to about 85° C., preferably about 60° to about 75° C.

Various polymerization initiators are usable which are known for use in preparing polyacrylates. Examples of useful initiators are redox initiators comprising a reducing agent, such as a sulfite or bisulfite of an alkali metal, ammonium sulfite or ammonium bisulfite, and an initiator, such as a persulfate of an alkali metal or ammonium persulfate, in combination with the reducing agent; azo initiators including azobis-isobutyronitrile, 4-t-butylazo-4'-cyanovaleric acid (V-50), 4,4'-azobis(4-cyanovaleric acid) and 2,2'-azobis(2-amidinopropane)-hydrochloric acid salt; and the like. These initiators can be used singly or in a suitable combination. Of these, especially preferable are a redox initiator composed of ammonium persulfate and sodium hydrogensulfite, and azo initiators such as azobisisobutyronitrile and 2,2'-azobis(2-amidinopropane)-hydrochloric acid. The initiators are advantageously used usually in the form of an aqueous solution but can be used as diluted with a suitable solvent. The initiator is used in a usual amount, i.e., in an amount, calculated as solids, of about 0.1 to about 10%, preferably about 0.5 to about 5%, of the combined weight of the monomers, namely acrylate (and free acrylic acid); styrene and/or methyl methacrylate; acrylamide; and polyvinyl monomer cross-linking agent. Depending on the amount and kind of the initiator, the initiator is usable together with isopropyl alcohol, alkylmercaptan or other chain transfer agents to control the molecular weight of the polyacrylate copolymer to be obtained.

By the addition of the polymerization initiator, the mixed monomer solution is subjected to copolymerization with evaporation of water without heating the system from outside. More advantageously, the reaction is carried out by admixing a predetermined amount of the initiator or an aqueous solution thereof with the mixed monomer solution and causing the resulting mixture to flow down onto and spread over a traveling conveyor belt or reacted continuously. The initiator can be added to the mixed monomer solution as it is poured onto the conveyor belt.

The copolymerization proceeds rapidly after admixing the initiator with the mixed monomer solution and is completed within a short period of time, usually in about 30 seconds to about 10 minutes. The reaction is exothermic, so that the reaction system is rapidly heated to about 100° to about 130° C. by the heat of polymerization. Consequently, particularly where the monomer concentration in the mixed solution is at least 50 percent by weight, the water evaporates from the system rapidly to give a relatively dry, solid copolymer of low water content without resorting to any external heating. The water content of the copolymer is usually up to about 15%, and generally about 8 to 12% by weight as recovered. Subsequently, the dry solid copolymer can be made into the desired powder easily by a usual method, for example by pulverization, without a drying step.

In accordance with another important feature of the present invention, polystyrene and/or methylcellulose can be added to the mixed monomer solution in an amount of 0.5 to about 10 percent based on the total weight of monomers in the mixed monomer solution to increase the porosity and water absorbing capacity of the copolymers. It has been found, quite surprisingly, the polystyrene and methylcellulose will substantially increase the water absorbing capacity of the resin copolymer described herein. To achieve the full advantage of the present invention, the polystyrene and methylcellulose should be added in an average grain size of less than or equal to 5 micrometers.

The powder thus obtained has outstanding water absorbing ability and is useful for sanitary goods, paper diapers, disposable diapers and like hygenic goods, agricultural or horticultural water retaining agents, industrial dehydrating agents, sludge coagulants, thickening agents, condensation preventing agents for building materials, release control agents for chemicals and various other applications.

In accordance with a new and unexpected feature of the present invention, it has been found that by copolymerizing partially neutralized or fully neutralized acrylic acid with styrene and/or methyl methacrylate, the total absorbency of the resulting copolymer as well as the retention capacity of the copolymer is unexpectedly superior to the absorbent homopolymer made without styrene or methyl methacrylate. Further, in accordance with another new and unexpected feature of the present invention, when the styrene and/or methyl methacrylate is included in the mixed monomer solution in an amount of 5–25% based on the weight of acrylic acid and acrylate (computed based on the molecular weight of acrylic acid), the initial rate of the water absorption of the resulting copolymer is unexpectedly superior to the homopolymer manufactured without the styrene and/or methyl methacrylate copolymerization. It appears that when the styrene and/or methyl methacrylate is added to the mixed monomer solution in an amount of 1 to about 5% based on the weight of acrylic acid, only the total water absorption and total water retention is increased. However, when the styrene and/or methyl methacrylate is added to the mixed monomer solution in amount of about 5% to about 25% based on the weight of acrylic acid, not only is the total water absorption and the total water retention far superior to that of the homopolymer, but the initial rate of water absorption is far superior to that of the acrylic homopolymer and to that of the acrylic acid acrylamide copolymer.

Figure 1:
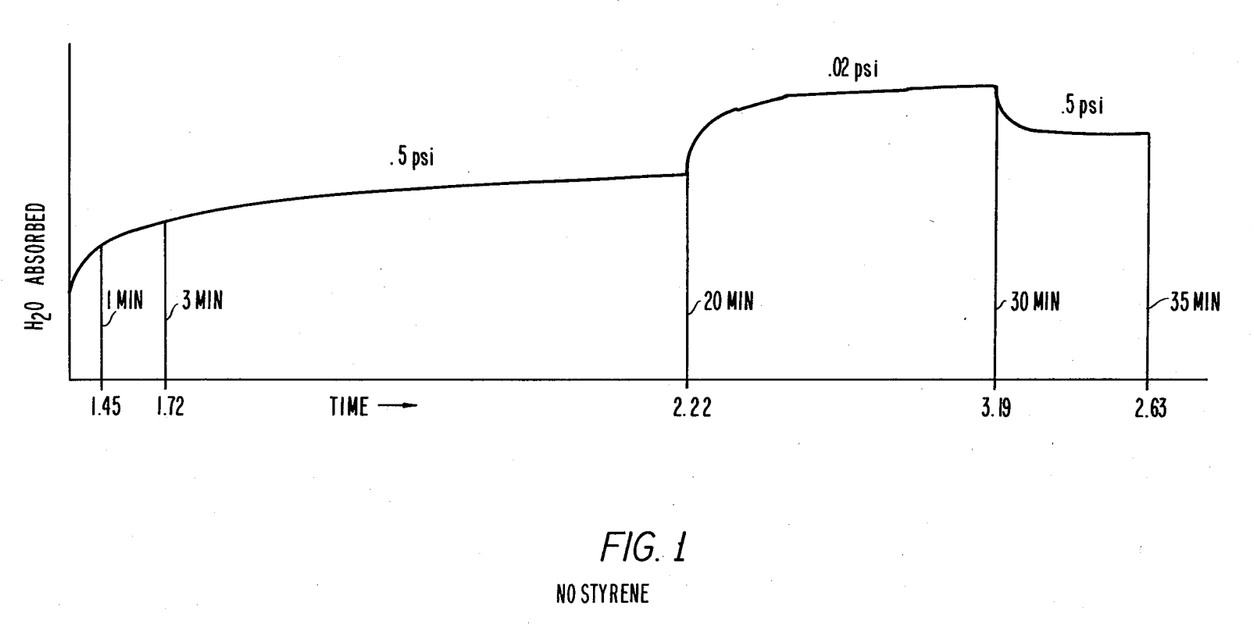
FIG. 1 is a graph obtained using a gravimetric absorbancy system (GATS) showing the water absorbancy vs. time for an acrylic homopolymer.

In order to show the new and unexpected results achieved by the co- or ter-polymerization of partially or fully neutralized acrylic acid with styrene and/or methyl methacrylate, the water absorption and retention properties of an acrylic acid homopolymer was studied, as shown in FIG. 1. The acrylate homopolymer was prepared in the same manner as described with respect to Example 1 using the following mixed monomer solution:

| CHEMICAL | PARTS BY WEIGHT | PERCENT |
|---|---|---|
| Acrylic Acid | 16.80 | 54.15 |
| Ammonium hydroxide (30% aqueous ammonia) | 4.20 | 13.54 |
| Potassium hydroxide | 4.20 | 13.54 |
| Azo cross-linking agent | 0.13 | 0.42 |
| GPTA (glycerol propoxy triacrylate molecular weight 428.5) | 0.002 | 0.01 |
| Ammonium carbonate | 3.31 | 10.67 |
| $H_2O$ | 2.30 | 7.67 |

The results shown in FIG. 1 were obtained using a gravometric absorbency testing system (GATS). The polymer made in accordance with Example 1 using the mixed monomer solution listed above is placed in contact with water under a retaining disc exerting 0.5 psi pressure on the polymer for 20 minutes to determine an initial rate of water absorption and, after 20 minutes, the pressure above the polymer is reduced to 0.02 psi with a lighter retaining disc for 10 minutes to determine a total water absorption. At a 30 minute time interval, the pressure above the polymer is again increased to 0.5 psi to determine a total amount of water retained by the polymer. Water absorption readings determined by increase in polymer rate were taken at the 1 and 3 minute time periods to determine an initial rate of water absorption. A reading was taken at the 20 minute time interval to determine the total water absorbed under the 0.5 psi retaining disc and water absorption readings taken at the 30 minute time interval to determine the total water absorbed by the polymer. Readings taken at a 35 minute time interval with the 0.5 psi retaining weight on the polymer were taken to determine the total amount of water retained by the polymer. The readings on the lower coordinate, or x axis of the graph of FIG. 1 represent the grams of water absorbed per 0.1 gram of polymer and are as follows: 1 minute, 1.45; 3 minutes 1.72; 20 minutes, 2.22; 30 minutes, 3.19, 35 minutes, 2.63.

Figure 2:
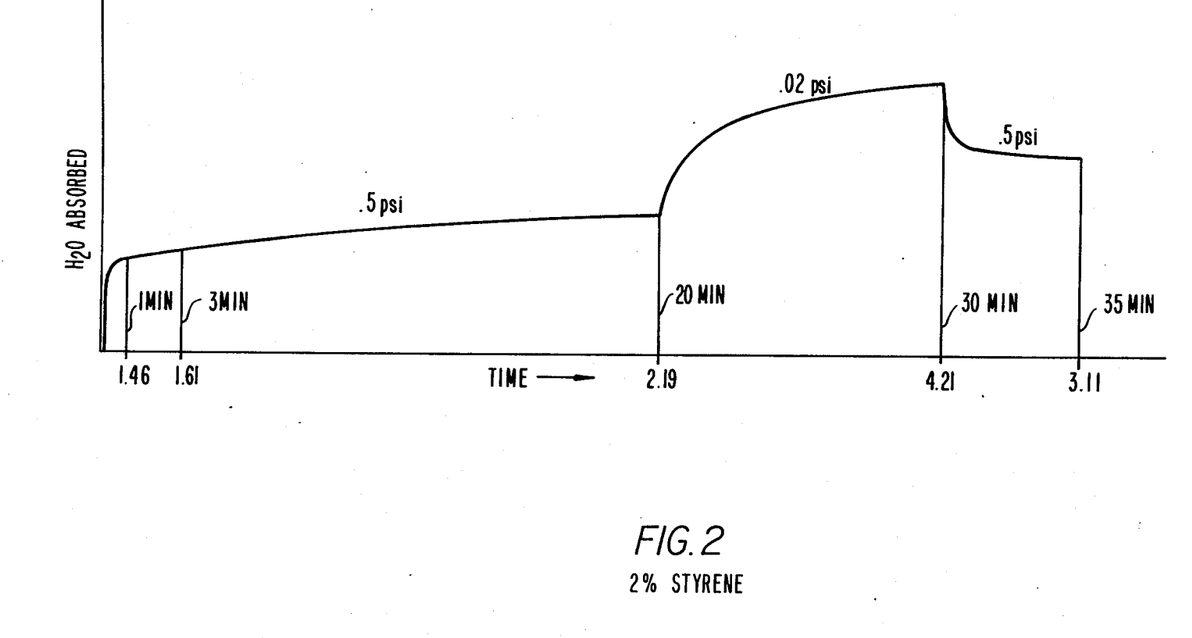
FIG. 2 is a graph obtained using a gravimetric absorbancy system (GATS) showing the water absorbancy vs. time for an acrylic-styrene copolymer having 2% styrene.
Figure 3:
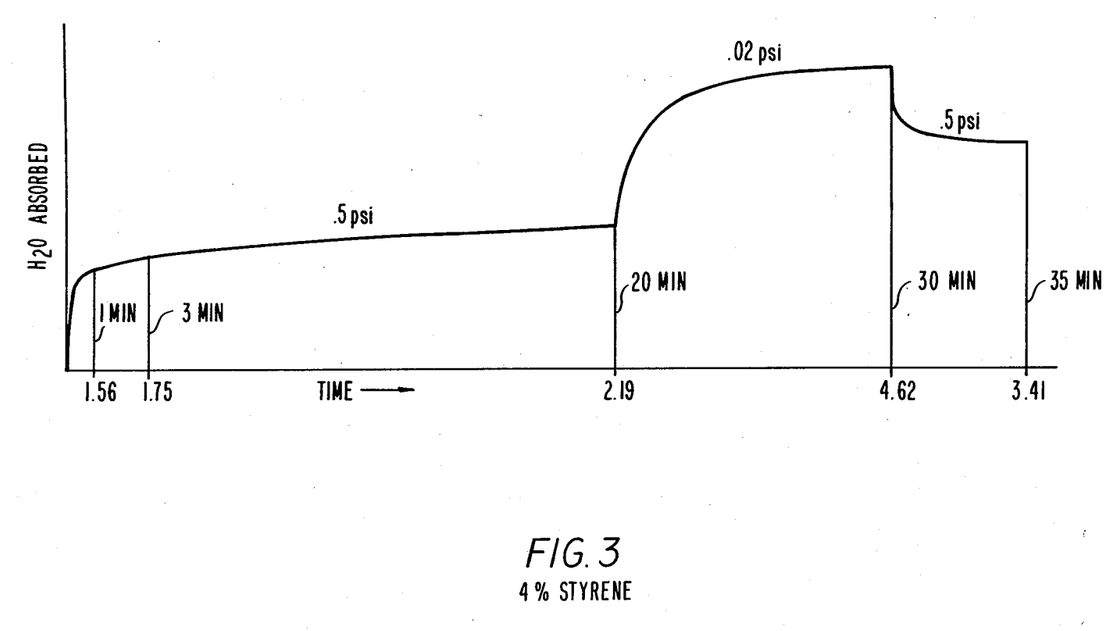
FIGS. 3 and 4 are graphs obtained using a gravimetric absorbancy system (GATS) showing the water absorbancy vs. time for acrylic-styrene copolymers having 4% and 6% styrene, respectively.
Figure 4:
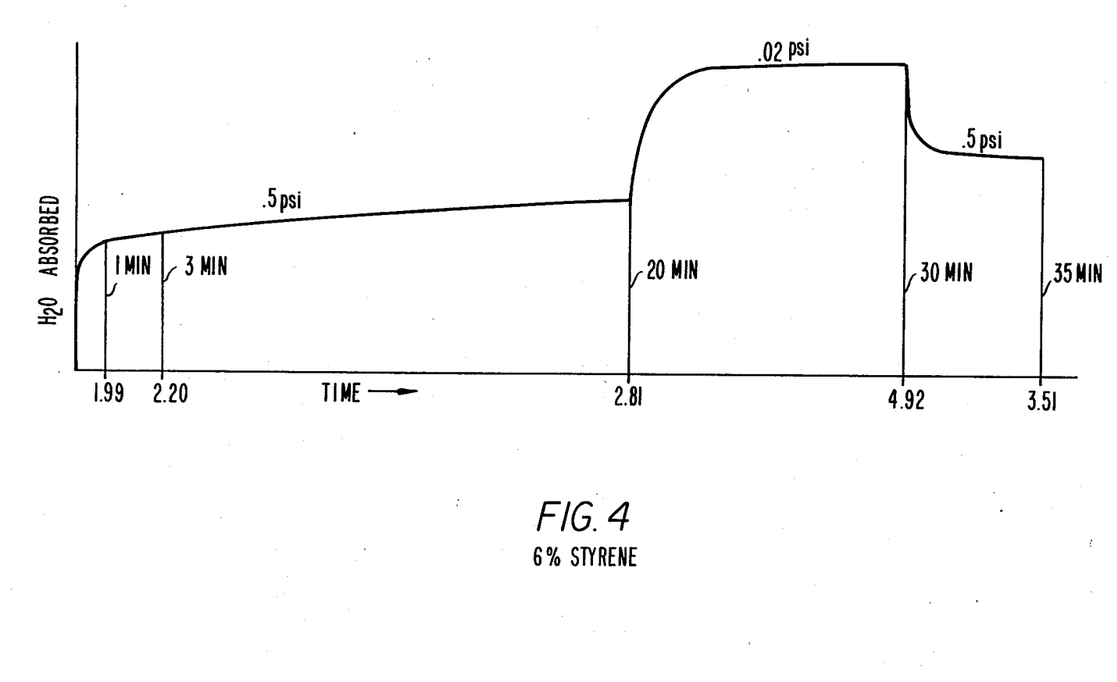

This same procedure outlined above was used to determine initial water retention, total water retention and total absorbency of the copolymers or terpolymers of the present invention wherein the acrylate is copolymerized with styrene and/or methyl methacrylate, as shown in FIGS. 2–4. The copolymer of FIG. 2 was prepared in the same manner as that of FIG. 1 except with the addition of styrene by copolymerizing the following mixed monomer composition:

| CHEMICAL | PARTS BY WT. | PERCENT |
|---|---|---|
| Acrylic Acid | 16.80 | 53.57 |
| Ammonium Hydroxide (70% $H_2O$) | 4.20 | 13.39 |
| KOH solid | 4.20 | 13.39 |
| Styrene | 0.81 | 1.08 |
| V-50 | 0.13 | 0.42 |
| GPTA (glyceryl propoxytriacrylate) MW = 428.5 | 0.002 | 0.01 |
| $(NH_4)_2CO_3$ solid | 3.31 | 10.55 |
| $H_2O$ | 2.38 | 7.59 |
| TOTAL | 31.36 | 100.0 |

As shown in FIG. 2, when the mixed monomer solution contains 2% styrene based on the weight of acrylic acid, the total water absorbency measured at the 30 minute time interval increased from a value of 3.19 (see FIG. 1 homopolymer data) to a value of 4.21 and the total amount of water retained increased from a value of 2.63 (see FIG. 1 homopolymer data) to a value of 3.11 representing an increase in total water absorbed of more than 30% and an increase in total water retention of almost 20%. These results, and similar results shown in FIGS. 3 and 4 (4% and 6% styrene, respectively), are most surprising in the art of water absorbant polymers.

The present invention will be described in greater detail with reference to the following examples.

EXAMPLE 1

The following are combined, wherein percents are weight percents based on the total weight of the monomer solution formed, 59.99% acrylic acid first, then 12.12% potassium hydroxide and 12.12% ammonium carbonate and 15.15% ammonium hydroxide serving as neutralizing agents and 1% styrene based on the weight of acrylic acid. Thereafter 0.03% of N,N-methylenebisacrylamide as a polyvinyl monomer is added to prepare an aqueous solution of potassium acrylate and ammonium acrylate which is 23.84% water having a neutralization degree of about 90% and a combined monomer concentration of 60.58 wt. %.

The aqueous solution is maintained at 70° C., and with the solution is admixed 0.15% of 2,2¹- azobis-(2-amidino-propane)hydrochloric acid in an aqueous solution. The final solution is as follows:

| CHEMICALS | |
|---|---|
| ACRYLIC ACID | 58.23% |
| STYRENE | 0.58% |
| POTASSIUM HYDROXIDE | 11.76% |
| AMMONIUM CARBONATE | 11.76% |
| N,N—METHYLENEBISACRYLAMIDE | 0.03% |
| AZO POLYMERIZATION INITIATORS (5% wt. aqueous) | 0.15% |
| AMMONIUM HYDROXIDE (30% wt. aqueous ammonia)) | 14.70% |
| H₂O | 2.79% |
| TOTAL | 100.00 |

The mixture is poured onto a traveling endless belt and spread thereover in the form of a layer about 10 mm in thickness. About 30 seconds thereafter, the mixture starts to polymerize, and the reaction is completed in about 1 minute. The maximum temperature of the mixture during the reaction is about 120° C.

The copolymer is allowed to complete curing for about 30 minutes at ambient temperature to give a dry solid strip of potassium/ammonium polyacrylate and polyacrylic-polystyrene product having a water content of 11% and a residual monomer concentration of 1200 ppm. The strip is made into a powder by a pulverizer.

EXAMPLES 2 TO 5

Copolymers are prepared in the same manner as in Example 1 with the exception of varying at least one of the combined concentration of monomers, the amount of polyvinyl monomer (N,N-methylenebisacrylamide), the kind and amount (degree of neutralization) of neutralizing agent, and the amounts based on the combined amount of the monomers, of azo polymerization initiator. The following compositions are copoly- merizable:

EXAMPLE 2

| ACRYLIC ACID | 56.01% |
|---|---|
| STYRENE | 2.80% |
| POTASSIUM HYDROXIDE | 11.76% |
| AMMONIUM CARBONATE | 11.76% |
| N,N—METHYLENEBISACRYLAMIDE | 0.03% |
| AZO POLYMERIZATION INITIATOR (5% wt. aqueous) | 0.15% |
| AMMONIUM HYDROXIDE (30% wt. aqueous ammonia) | 14.70% |
| H₂O | 2.79% |
| TOTAL | 100.00% |

EXAMPLE 3

| ACRYLIC ACID | 56.80% |
|---|---|
| STYRENE | |
| POTASSIUM HYDROXIDE | 14.77% |
| AMMONIUM CARBONATE | 11.36% |
| N,N—METHYLENEBISACRYLAMIDE | 0.03% |
| AZO POLYMERIZATION INITIATOR (5% wt. aqueous) | 0.14% |
| AMMONIUM HYDROXIDE (30% wt. aqueous ammonia) | 14.20% |
| H₂O | 2.70% |
| TOTAL | 100.00% |

EXAMPLE 4

| ACRYLIC ACID | 57.13% |
|---|---|
| STYRENE | |
| POTASSIUM HYDROXIDE | 14.28% |
| AMMONIUM CARBONATE | 11.43% |
| N,N—METHYLENEBISACRYLAMIDE | 0.03% |
| AZO POLYMERIZATION INITIATOR (5% wt. aqueous) | 0.14% |
| AMMONIUM HYDROXIDE (30% wt. aqueous ammonia) | 14.28% |
| H₂O | 2.71% |
| TOTAL | 100.00% |

EXAMPLE 5

| ACRYLIC ACID | 54.66% |
|---|---|
| STYRENE | |
| POTASSIUM HYDROXIDE | 10.93% |
| AMMONIUM CARBONATE | |
| N,N—METHYLENEBISACRYLAMIDE | 0.11% |
| AZO POLYMERIZATION INITIATOR (5% wt. aqueous) | 0.41% |
| AMMONIUM HYDROXIDE (30% wt. aqueous) | 30.61% |
| H₂O | 3.28% |
| TOTAL | 100.00% |

The amount of polyvinyl monomer listed is expressed in % by weight based on the combined amount of potassium acrylate, free acrylic acid, styrene and the polyvinyl monomer, and the concentration of initiator is expressed in % by weight based on the combined amount by weight (calculated as solids) of the monomers and the initiator, the same as hereinbefore.

EXAMPLE 6

To 22.2 g of deionized water are added 72.1 g of acrylic acid first, then 49.5 g of potassium hydroxide having a purity of 85% and serving as a neutralizing agent, and thereafter 3.0 grams of styrene and 0.01 g of N,N-methylenebisacrylamide as a polyvinyl monomer to prepare an aqueous solution of potassium acrylate having a neutralization degree of 75%, styrene, and a combined monomer concentration of about 75 wt. %.

The aqueous solution is maintained at 70° C., and with the solution are admixed 2.9 g of 18% aqueous solution of ammonium persulfate (0.67 wt. % based on the combined weight of the potassium acrylate, free acrylic acid styrene and N,N-methylenebisacrylamide, the same as hereinafter). The mixture is poured onto a traveling endless belt and spread thereover in the form of a layer about 10 mm in thickness. About 30 seconds thereafter, the mixture starts to polymerize, and the reaction is completed in about 1 minute. The maximum temperature of the mixture during the reaction is about 120° C.

The reaction gives a dry solid strip of cross-linked potassium polyacrylate-styrene copolymer product. The strip is made into a powder by a pulverizer.

EXAMPLES 7 TO 10

Polymers are prepared in the same manner as in Example 6 with the exception of changing at least one of the amount of N,N-methylenebisacrylamide and the kind and amount of the polymerization initiator as listed in Table 1 below.

TABLE 1

| Ex. No. | Initiator Kind | Conc. | Amt. of Polyvinyl Monomer |
|---|---|---|---|
| 7 | 2,2'-azobis-(2-amidino-propane) hydrochloric acid | 0.5 | 0.01 |
| 8 | 2,2'-azobis-(2-amidino-propane) hydrochloric acid | 0.5 | 0.02 |
| 9 | 2,2'-azobis-(2-amidino-propane) hydrochloric acid | 1.0 | 0.01 |
| 10 | 2,2'-azobis-(2-amidino-propane) hydrochloric acid | 1.0 | 0.02 |

EXAMPLES 11 TO 18

Polymers are prepared in the same manner as in Example 1 except that the compounds listed in Table 2 below are used as polyvinyl monomers in the listed amounts.

TABLE 2

| Ex. No. | Polyvinyl Monomer Kind | Amount |
|---|---|---|
| 11 | Ethylene glycol diallyl ester | 0.01 |
| 12 | " | 0.02 |
| 13 | Diethylenetriamine-diacrylamide | 0.01 |
| 14 | " | 0.02 |
| 15 | N,N—methylenebismethacrylamide | 0.01 |
| 16 | " | 0.05 |
| 17 | Polyethylene glycol diacrylate* | 0.01 |
| 18 | " | 0.05 |

*Polyethylene glycol diacrylate used in Examples 17 and 18 is represented by the following formula:

EXAMPLES 19 TO 22

Acrylic acid (72.1 g), 18.0 g of deionized water, 40.9 g of solid potassium hydroxide (water content 4%) 3.0 grams methyl methacrylate, and 5.2 g acetone (5 wt. % based on the monomers) are mixed together, and the mixture is maintained at 75° C. With the mixture is further admixed 4.0 g of 10% aqueous solution of 2,2'-azobis(2-amidinopropane)hydrochloric acid salt. The resulting mixture is immediately poured onto a traveling endless belt and spread thereover to a thickness of 5 mm. About 15 seconds later, the mixture starts to polymerize, and the polymerization is completed in about 30 seconds. The maximum temperature of the mixture during the reaction of 130° to 135° C.

The reaction gives a dry strip of cross-linked potassium polyacrylate product, which is pulverized to a powder 20 to 100 mesh in particle size.

The same procedure as above is repeated with use of the other solvents.

EXAMPLE 23

An aqueous monomer solution is prepared in the same manner as in examples 19 to 22 with the exception of not using any organic solvent and using 23.2 g of deionized water. The solution is thereafter subjected to polymerization in the same manner as in these examples to obtain a powder of dry solid.

EXAMPLES 24 TO 26

Water absorbing resin solids are prepared in the same manner as in Example 19 with the exception of using 3, 5 or 10 wt. %, based on the monomers, of methanol in place of 5.2 g of acetone and varying the amount of deionized water so that the combined amount of the water and the methanol is 23.2 g.

EXAMPLE 27

281. gr. of acrylic acid and 11.9 gr. of acrylamide are dissolved in 179.1 gr. of distilled water and then 10.9 gr. of NaOH is added for 70 mole percent partial neutralization of acrylic acid; 3 grams of methyl methacrylate; 0.003 gr. of N,N'-methylenebisacrylamide is then added as the polyvinyl monomer. In this case, 0.04 gr. of 2,2'-azobis(2-amidinopropane)hydrochloride is added as the polymerization initiator and the initial temperature of the mixed monomer solution is 50° C.

EXAMPLES 28

48.1 gr. of acrylic acid and 11.9 gr. of acrylamide are dissolved in 159 gr. of distilled water and then 22.7 gr. of NaOH is added for partial neutralization of acrylic acid in an amount of 85 mole percent. 3.0 grams of styrene then is added. 0.006 gr. of N,N'-methylenebisacrylamide is then added as the polyvinyl monomer. In addition, 0.048 gr. of ammonium persulfate and 0.048 gr. of sodium hydrogensulfite are added as the polymerization initiators. In this case, the initial temperature of the mixed monomer solution is 40° C.

EXAMPLE 29

90.1 gr. of acrylic acid and 9.9 gr. of acrylamide are dissolved in 118.8 gr. of distilled water and 52.6 gr. of KOH is added for 75 mole percent partial neutralization of acrylic acid. 2 grams of styrene is added to the solution. 0.018 gr. of N,N'-methylenebisacrylamide is added as the polyvinyl monomer, and 0.08 gr. of ammonium persulfate and 0.08 gr. of sodium hydrogen-sulfite are added as the polymerization initiators. The initial temperature of the mixed monomer solution is 30° C.

EXAMPLE 30

48.1 gr. of acrylic acid and 11.9 gr. of acrylamide are dissolved in 252.1 gr. of distilled water and 27.4 gr. of aqueous ammonia is added for 70 mole percent partial neutralization of acrylic acid. In this case, the concentration of the ammonia is 29 weight percent. In addition, one gram of methyl methacrylate and 0.006 gr. of N,N'-methylenebisacrylamide are added. The polymerization is performed with the addition of 0.048 gr. of ammonium persulfate and 0.048 gr of sodium hydrogen-sulfite for initiation. In this case, the initial temperature of the mixed monomer solution is 30° C.

EXAMPLE 31

52.7 gr. of acrylic acid and 17.3 gr. of acrylamide are dissolved in 25 gr. of distilled water and they are partially neutralized 80 mole percent with the addition of 32.8 gr. of KOH. 2.5 grams of styrene and 0.007 gr. of N,N'-methylenebisacrylamide is added. For the polymerization catalyst 0.7 gr. of 2,2'-azobisisobutyronitrile dissolved in 10 cc. of acetone is added. The solution is kept at 80° C. in a TEFLON coated, glass fiber reaction chamber until completion of polymerization and cross-linking reactions yielding a solid resin.

EXAMPLE 32

17.3 gr. of acrylamide is dissolved in 52.7 gr. of acrylic acid and partial (70 mole percent) neutralization of acrylic acid is accomplished by the addition of 30 gr. of aqueous ammonia having a concentration of 29 weight percent. In this case, for the polyvinyl monomer, 0.007 gr. of N,N'-methylenebisacrylamide is added. 0.7 grams of styrene is added for copolymerization and, as the catalyst, 0.7 gr. of 2,2'-azobis(2-amidinopropane)hydrochloride dissolved in 8 gr. of distilled water is added. The polymerization is started at 80° C. to yield a solid resin.

EXAMPLE 33

21 kg. of acrylic acid and 7 kg. of acrylamide are dissolved in 9.5 kg. of distilled water and the acrylic acid is partially neutralized with 12 kg. of KOH. 0.036 kg. of methylenebisacrylamide as a polyvinyl monomer was added as well as one gram of styrene and one gram of methyl methacrylate to provide an aqueous mixed monomer solution. The mixed monomer solution is mixed with 0.28 kg. of 2,2'-azobisisobutyronitrile, dissolved in 2 kg. of acetone as a polymerization initiator. This mixture at a temperature of 60° C. is transferred on an endless belt (600–700 mm. in width, and 7 m. in length) at a thickness of about 1 cm. The polymerization is initiated promptly on the belt resulting in a solid resin.

EXAMPLE 34

52.7 gr. of acrylic acid and 17.3 gr. of acrylamide are dissolved in 20 gr. of distilled water. 32.8 gr. of KOH is added for 80 mole percent partial neutralization of acrylic acid. Then 0.007 gr. of N,N'-methylenebisacrylamide polyvinyl monomer is added with 2.6 gr. of methylcellulose. The aqueous monomer mixture is homogenized with agitation. Next, as an initiator, 0.7 gr. of 2,2'-azobisisobutyronitrile dissolved in 10 cc of acetone is added. This mixed solution is kept at 80° C. in a water bath surrounding the reaction chamber. Polymerization is initiated as the temperature of the mixture increases as a result of the surrounding water bath, resulting in a solid porous resin.

EXAMPLE 35

120.8 gr. of acrylamide is dissolved in 49.2 gr. of acrylic acid and 28.0 gr. of aqueous ammonia (29% concentration) is added for 70 mole percent neutralization of the acrylic acid. Next, 0.01 gr. of N,N'-methylenebisacrylamide, 3.5 grams of styrene and 5 gr. of methylcellulose are added and stirred to homogenize. As an initiator, 0.7 gr. of 2,2'-azobis(2-amidinopropane)-hydrochloride dissolved in 5 gr. of distilled water is added. The polymerization is initiated in a TEFLON coated glass reaction chamber kept at 80° C., yielding a solid porous resin having a water content of less than 15% by weight.

EXAMPLE 36

70 gr. of acrylic acid is dissolved in 20 gr. of distilled water. 40.8 gr. of KOH is added to neutralize 75 mole percent of the acrylic acid. Next, 0.007 gr. of N,N'-methylenebisacrylamide, 3 grams of methyl methacrylate and 2.0 gr. of methylcellulose are added, and the mixture homogenized with agitation. Then, as an initiator, 0.7 gr. of 2,2'-azobisisobutyronitrile dissolved in 10 cc. of acetone is added. This solution is transferred to the reaction chamber kept at 80° C. and polymerization is initiated with a rise in temperature of the mixture resulting in a solid porous resin of low water content.

EXAMPLE 37

Same as Example No. 34, but having no methylcellulose.

EXAMPLE 38

Same as Example No. 35, but having no methylcellulose.

EXAMPLE 39

Same as Example No. 36, but having no methylcellulose.

EXAMPLE 40

52.7 gr. of acrylic acid and 17.3 gr. of acrylamide are dissolved in 20 gr. of distilled water. 32.8 gr. of potassium hydroxide is added to neutralize 80 mole percent of the acrylic acid. Next, 2.5 grams of styrene, 0.007 gr. of N,N'-methylenebisacrylamide, and 5 gr. of a polystyrene emulsion are added and homogenized under stirring. The polystyrene emulsion has a concentration of 50 weight percent and a polystyrene grain size of about 0.5 micro meters. Then, as the initiator, 0.7 gr. of 2,2'-azobisisobutyronitrile dissolved in 10 cc of acetone solution is added. The mixed monomer solution is kept at 80° C. in the reaction chamber immersed in a water bath. With the increasing temperature of the mixed monomer solution polymerization is initiated resulting in a solid, porous resin.

EXAMPLE 41

20.8 gr. of acrylamide is dissolved in 49.2 gr. of acrylic acid. 28.0 gr. of aqueous ammonia (29% concentration) is added to neutralize 70 mole percent of the acrylic acid. Then 10 grams of styrene and 0.01 gr. of N,N'-methylenebisacrylamide are added. 3 gr. of the polystyrene emulsion of Example 40, but having a 1 micro meter average grain size, is added and the mixed solution is homogenized with agitation. Next, as the initiator, 0.7 gr. of 2,2'-azobis(2-amidinopropane)- hydrochloride dissolved in 5 gr. of distilled water is added. The solution is kept at 80° C. and polymerization is initiated with increased temperature resulting in a solid, porous resin.

EXAMPLE 42

70 gr. of acrylic acid is dissolved in 20 gr. of distilled water and 40.8 gr. of KOH is added to neutralize 75 mole % of the acrylic acid. Next, 10 grams of methyl methacrylate and 0.007 gr. of N,N'-methylenebisacrylamide are added. 2 gr. of the polystyrene emulsion of Example 40 (but having an average grain size of 5 micrometers), is added and the mixture homogenized. Next, as the initiator, 0.7 gr. of 2,2'-azobisisobutyronitrile dissolved in 10 cc. of acetone is added. The mixed solution is kept at 90° C. in the water bath to initiate the polymerization resulting in a solid, porouos resin.

EXAMPLE 43

Same as Example 40, but having no polystyrene.

EXAMPLE 44

Same as Example 41, but having no polystyrene.

We claim:

1. A process for preparing a solid water absorbing resin comprising mixing a monomer solution of (A) acrylic acid neutralized 70-100 mole percent; (B) styrene in an amount of 1% to 25% based on the weight of acrylic acid and (C) a water-miscible to water-soluble polyvinyl monomer in a combined concentration of (A), (B) and (C) of at least 30 wt. %; with water to form a mixed monomer solution wherein the monomers of the mixed monomer solution consist essentially of (A) and (B) and (C) and initiating polymerization of monomers (A), (B) and (C) such that during polymerization, the exothermic heat of reaction is substantially the only heat energy used to accomplish polymerization, cross-linking and to drive off sufficient water to obtain a solid cross-linked resin having a water content of 15 percent by weight or less.

2. A process as defined in claim 1 wherein the combined concentration of the monomers (A), (B) and (C) is at least 30 wt. % and less than 70 wt. %.

3. A process as defined in claim 1 wherein the mixed monomer solution has a temperature of 20° to 85° C. prior to polymerization.

4. A process as defined in claim 1 wherein monomer (C) is selected from the group consisting of N,N-methylenebisacrylamide and N,N-methylenebismethacrylamide.

5. A process as defined in claim 1 wherein the mixed monomer solution contains 1 to 10 wt. % of an organic solvent based on the weight of monomers (A), (B) and (C).

6. A process as defined in claim 1 wherein the mixed monomer solution further contains an organic solvent having a boiling point of 40° to 150° C.

7. A process for preparing a solid, water absorbing, cross-linked resin comprising:
combining a monomer mixture of (A) potassium acrylate; (B) styrene in an amount of 1% to 25% based on the amount of acrylate computed based on the weight of acrylic acid; and (C) a polyvinyl monomer, with water in an amount of at least 30 combined weight percent of (A) plus (B) plus (C) based on the total weight of (A) plus (B) plus (C) plus water to form a monomer mixture wherein the monomers of the the monomer mixture consist essentially of (A), (B) and (C);
adding a polymerization initiator to said monomer mixture capable of initiating, and in an amount sufficient to initiate polymerization of said monomer mixture;
copolymerizing said monomer mixture while utilizing the exothermic heat of reaction as substantially the only non-ambient energy source to drive water away from said polyacrylate resin copolymer to form said cross-linked resin copolymer having a water content sufficiently low to be powdered without an intermediate drying step.

8. The process of claim 7 further including the step of adjusting the temperature of the monomer mixture to a temperature of 25° to 85° C. prior to adding said polymerization initiator to said monomer mixture.

9. The process of claim 8 wherein said polymerization initiator is added in an amount of at least 0.5% total by weight of monomers (A), (B) and (C).

10. The process of claim 8 wherein the water content of said cross-linked resin copolymer is not greater than about 10% by weight as recovered from the polymerized mixture, without an additional drying step.

11. The process of claim 8 further including combining a non-aqueous solvent having a boiling point of 40°-150° C. with said monomers (A), (B) and (C) to form a porous resin.

12. The process of claim 8 including the step of pulverizing said cross-linked resin to form a powder.

13. A method of manufacturing a resin composition comprising mixing a monomer solution of (A) acrylic acid, neutralized 70 to 100 mole percent, (B) styrene in an amount of 1% to 25% based on the weight of acrylic acid and (C) acrylamide in a mole ratio of (A):(C) in the range of 70:30 to 100:0; (D) a water soluble or water miscible polyvinyl monomer cross-linking agent in an amount of 0.001 to 0.3 percent by weight of (A) plus (B) plus (C); and water to form a mixed monomer solution, wherein the monomers of the mixed monomer solution consist essentially of (A), (B), (C) and (D); and initiating polymerization of monomers (A), (B) and (C) such that during polymerization, the exothermic heat of reaction is substantially the only heat energy used to accomplish polymerization, cross-linking and to drive off sufficient water to form a water absorbing cross-linked polyacrylate resin composition having a water content of 15 percent by weight or less.

14. The method of claim 13 wherein the water content of said cross-linked polyacrylate resin copolymer is not greater than about 10% by weight as recovered from the mixed monomer solution after copolymerization, without an additional drying step.

15. The method of claim 13 including depositing said monomer mixture including said initiator onto a support surface in sheet form for polymerization and cross-linking.

16. A method of absorbing water comprising mixing a monomer solution of (A) acrylic acid, neutralized 70 to 100 mole percent, (B) styrene in an amount of 1% to 25% based on the weight of acrylic acid and (C) acrylamide in a mole ratio of acrylic acid: acrylamide in the range of 70:30 to 100:0; (D) a water soluble or water miscible polyvinyl monomer cross-linking agent in an amount of 0.001 to 0.3 percent by weight of (A) plus (B) plus (C); and water to form a mixed monomer solution, wherein the monomers of the mixed monomer solution consist essentially of (A), (B), (C) and (D) and the monomer concentration is below 70 percent by weight of the monomer solution prior to polymerization initiation; and initiating polymerization of monomers (A) and (B) such that during polymerization, the exothermic heat of reaction is substantially the only heat energy used to accomplish polymerization, cross-linking and to drive off sufficient water to form a water absorbing cross-linked polyacrylate resin having a water content of 15 percent by weight or less, and thereafter contacting said resin with water to absorb water into said resin.

* * * * *